US006386016B1

(12) United States Patent
Gleissle (10) Patent No.: US 6,386,016 B1
(45) Date of Patent: May 14, 2002

(54) METHOD AND DEVICE FOR SIMULTANEOUS DETERMINATION OF SHEAR VISCOSITY AND EXTENSIONAL VISCOSITY

(75) Inventor: Wolfgang Gleissle, Hagenbach (DE)

(73) Assignee: Thermo Haake GmbH, Karlsruhe (DE)

( * ) Notice: Subject to any disclaimer, the term of this patent is extended or adjusted under 35 U.S.C. 154(b) by 0 days.

(21) Appl. No.: 09/420,425

(22) Filed: Oct. 19, 1999

(30) Foreign Application Priority Data

Oct. 22, 1998 (DE) .......................... 198 48 687

(51) Int. Cl.$^7$ ..................... G01N 11/08; G01N 11/04
(52) U.S. Cl. ..................... 73/54.01; 73/54.06; 73/54.11
(58) Field of Search ............... 73/54.01, 54.05, 73/54.06, 54.09, 54.11

(56) References Cited

U.S. PATENT DOCUMENTS

| | | | | |
|---|---|---|---|---|
| 3,468,158 A | * | 9/1969 | Chien | 73/55 |
| 3,908,442 A | * | 9/1975 | Chmiel | 73/55 |
| 3,952,577 A | * | 4/1976 | Hayes | 73/55 |
| 4,157,029 A | * | 6/1979 | Leca | 73/55 |
| 4,425,790 A | * | 1/1984 | Bice et al. | 73/55 |
| 4,539,837 A | * | 9/1985 | Barnaby | 73/55 |
| 4,624,132 A | | 11/1986 | Parnaby | |
| 4,627,271 A | * | 12/1986 | Abbott et al. | 73/55 |
| 4,876,882 A | * | 10/1989 | Yau | 73/55 |
| 4,905,503 A | * | 3/1990 | Langrick | 73/55 |
| 5,357,784 A | | 10/1994 | Collier | |
| 5,394,738 A | * | 3/1995 | Bass et al. | 73/54.06 |
| 5,637,790 A | * | 6/1997 | de Corral | 73/54.06 |

FOREIGN PATENT DOCUMENTS

DE 42 36 407 A1 5/1994

* cited by examiner

*Primary Examiner*—Hezron Williams
*Assistant Examiner*—David J. Wiggins
(74) *Attorney, Agent, or Firm*—Paul Vincent (57) ABSTRACT

In a method for continuous or discontinuous measurement of shear and strain viscosities of Newtonian and non-Newtonian liquids, in particular structurally viscous liquids such as polymer melts and solutions and elastomers as well as other structural liquids, the liquid is passed through a first capillary or capillary configuration and through a second capillary connected in series therewith, wherein the liquid in the first capillary or capillary configuration shears only within a defined shear velocity range and the shear viscosity is determined, and, subsequently, the liquid in the second capillary having the same or somewhat smaller shear velocity range, shears and is additionally subjected to a strain-flow so that its flow-through resistance comprises shear as well as strain resistances. The flow-through resistance is determined by pressure measurements and, in order to separate out the strain viscosity, the pressure fraction of the shear flow resistance is extracted through subtraction of the portion of the pressure difference corresponding to this shear flow resistance using the measurements in the first capillary or capillary configuration.

33 Claims, 3 Drawing Sheets

Configuration A

Fig. 1

Configuration B

Fig. 2

Configuration A

Fig. 3a

Configuration B

Fig. 3b

Configuration A

Fig. 4a

Configuration B

METHOD AND DEVICE FOR SIMULTANEOUS DETERMINATION OF SHEAR VISCOSITY AND EXTENSIONAL VISCOSITY

This application claims Paris Convention priority of DE 198 48 687.1 filed Oct. 22, 1998 the complete disclosure of which is hereby incorporated by reference.

BACKGROUND OF THE INVENTION

Conventional continuous or discontinuous measuring capillary viscometers or rheometers determine the pressure difference between the input and the output of a measuring capillary having constant cross section through which a measuring liquid flows. The volume flow and the pressure differences can be used in conjunction with the dimensions of the capillary to determine a characteristic flow quantity (the "viscosity") for the liquid. The constant cross section of the capillary leads to pure shear flow and this "viscosity" is the shear viscosity $\eta$, $$\eta = \tau/\dot{\gamma} \tag{1}$$

where $\tau$ is the shear stress and $\dot{\gamma}$ the shear velocity. For Newtonian liquids whose shear viscosity is independent of the shear velocity, $\eta$ can be directly calculated from these measurements using conventional equations (Hagen-Poiseuille law).

A plurality of technical liquids (materials which occur in the liquid state during manufacturing processes) are non-Newtonian liquids whose viscosity depends on the shear velocity (for a given capillary dimension of volume flow). Principal examples therefor are primarily polymer melts and polymer solutions. In order to describe their flow behavior, viscosity functions or other flow functions, e.g. the shear-stress function, are required. The shear-stress function describes the shear stress in dependence on the shear velocity $\tau = f(\dot{\gamma})$. In a capillary rheometer of constant capillary cross section, only "apparent" viscosity values can be determined for these liquids, at constant volume flow, i.e. the Newtonian flow equation is utilized for the calculation.

In order to determined a flow function or parts of a flow function for process monitoring purposes, capillary rheometers have been used in recent times having wedge shaped or conical capillaries (see for example laid open publication DE-A-42 36 407, U.S. Pat. No. 4624 132 and A. Papendinskas, W. R. Cluett, S. T. Balke in Polymer Engineering and Science Mid-March 1991, Vol. 31. No. 5, pages 365–375). Capillary rheometers of this kind are equipped with pressure measuring probes to measure the pressure drop across parts of the capillary. Using e.g. a wedge-shaped capillary equipped with at least three pressure measuring locations, the actual non-Newtonian viscosity, for the shear velocity within the capillary, can be determined for constant operating conditions (e.g. $\dot{V}$=a constant or $\Delta p$=a constant). If, within the range of shear velocities occurring between the input and output of such a capillary, the flow function can be described using a simple flow law such as that given by Ostwald and de Waele (also referred to as the potential law) in accordance with equation (2) or (3) below, then the flow law is also known for these capillaries.

$$\tau(\dot{\gamma}) = K\dot{\gamma}^n \tag{2}$$

$$\eta(\dot{\gamma}) = K\dot{\gamma}^{n-1} = K\dot{\gamma}^m \tag{3}$$

Such rheometers are utilized for on-line processing and quality control and, when operated at constant pressure differentials, can even directly provide quantitative information concerning the average molecular weight and the molecular weight distribution (DE-A-42 36 407).

Capillary rheometers having such narrowing or widening capillaries do not however produce pure shear flow so that the result does not lead to a pure shear viscosity in all cases. In such capillaries, the shear flow is overlapped with an additional extensional flow (extension of an extrusion liquid in consequence of the cross section narrowing) and the overall flow resistance is a combination of shear and extensional components. Analogous to the shear resistance which results from the shear viscosity $\eta$ and the shear velocity $\dot{\gamma}$, the extensional resistance is caused by the extensional viscosity $\eta_E$ and the extensional velocity $\dot{\epsilon}$. The extensional resistance results from the tensile stress $\sigma$ produced in the flow. The extensional viscosity $$\eta E = \sigma/\dot{\epsilon} \tag{4}$$

is also designated Trouton-viscosity $\eta T$ and, for Newtonian liquids, is three times larger than the shear viscosity.

$$\eta T = 3\eta \tag{5}$$

In non-Newtonian liquids, in particular in plastic melts, this simple relationship as formulated in equation (5) is not satisfied. On the contrary, the ratio between $\eta_E$ and $\eta$ is often substantially more than three. In some fluids, $\eta_E$ is even an order of magnitude larger than $\eta$. The extent to which $\eta_E$ exceeds $\eta$ depends on the molecular properties and/or the molecular weight distribution of the plastic melt. In general, $\eta_E$ does not depend on $\eta$ and is only coupled to $\eta$ via molecular or structural properties. The extensional viscosity of high molecular liquids is particular sensitive to very small fractions of large molecules and on the degree of branching of the macro-molecules (K. K. Chao et al. AIChE J. 30 (1984), page 111 ff; J. Ferguson, M.K.H El-Tawashi Proc. VIII Int. Congr. on Rheol. Vol. II, page 235 ff). However, the degree of branching changes the viscosity function only to a limited extent and can therefore not be determined using the shear viscosity. If shear viscosity or shear viscosity functions can be measured in a particular process, information is thereby available concerning the average value and width of the molecular weight distribution of the liquid. If, in addition and independently thereof, the extensional viscosity can be determined, changes in the range of very large molecules and changes in the degree of branching can be detected with high sensitivity. An independent material quantity is therefore available which is definitive for specific liquid and product properties to better describe the quality of a product in a comprehensive and directed fashion.

It is the underlying purpose of the invention to create a method and a device with which the shear viscosity (e.g. in the range of 10 mPas$\leq \eta \leq 10^5$ Pas) and the extensional viscosity (e.g. in the range 30 mPas$\leq \eta_E \leq 10^8$ Pas) can be simultaneously determined on the same sample.

A method and apparatus with which the problem in accordance with the invention is solved is characterized in the patent claims.

SUMMARY OF THE INVENTION

Using a capillary having changing cross section and with a plurality of pressure measuring locations, the viscosity function of a liquid can be determined within a well defined shear velocity range under constant operating conditions (constant volume flow or pressure drop) (Papendinskas et al., DE-A-42 36 407). Although such capillaries do not have pure shear flow, the capillaries can be configured in such a fashion, e.g. having large length, that the influence of the extensional properties on the pressure drop is smaller than that of the shear properties by many orders of magnitude so that it can, in practice, be neglected. For a capillary of this type, the flow function is defined for the shear velocity range occurring between the input and the output.

The average extensional velocity $\bar{\epsilon}$ can be extracted from the difference between the average input and output velocities $\bar{V}_A - \bar{V}_E$, divided by the capillary length $\Delta L$ (Equation (6)):

$$\bar{\varepsilon} = \frac{\bar{V}_A - \bar{V}_E}{\Delta L} = \frac{\dot{V}/F_A - \dot{V}/F_E}{\Delta L} \quad (6)$$

The shear velocity $\dot{\gamma}_E$ and $\dot{\gamma}_A$ at the input and output are directly proportional to their average velocities $\bar{V}_E$ and $\bar{V}_A$ at the locations E and A, for constant cross section. A simple shortening of a wedge-shaped or conical capillary with otherwise constant input ($F_E$) and output ($F_A$) cross sections results, in accordance with equation (6), in a proportional increase in the average extensional velocity with constant shear velocity range between $\dot{\gamma}_E$ and $\dot{\gamma}_A$. It has however been determined in accordance with the invention, that different relationships for shear and extensional flow losses are established in capillaries having wedged shapes or conical shapes of differing length with however equal cross sections so that shear viscosities and extensional viscosities can be separated under certain conditions using flows having similar geometries.

In accordance with Papendinskas et al., the pressure drop due to shear viscosity for Newtonian or for potential liquids, across a wedge-shaped capillary for otherwise constant cross sections (i.e. equal shear velocities from $\dot{\gamma}_E$ to $\dot{\gamma}_A$), is directly proportional to the length of the capillary. Long capillaries therefore result in a larger viscous pressure drop. As can be seen from equation (6), long capillaries lead to a small extensional velocity $\bar{\epsilon}$ and, in accordance with equation (4), the tensile stress $\sigma$ is small. Long wedge-shaped or conical capillaries produce substantially viscous resistance and facilitate the direct determination of the viscosity or the viscosity function between the shear velocities $\dot{\gamma}_E$ and $\dot{\gamma}^A$.

A very short wedge-shaped or conical capillary having the same inlet and outlet cross sections as a long capillary produces, for constant volume flow, a lower pressure difference due to shear viscosity. However, the extensional velocity increases in accordance with equation (6) and the additional pressure difference resulting from this extensional viscosity increases strongly in comparison to the pressure loss due to shearing. The invention uses this realization in order to develop a method and a device with which the shear viscosity and the extensional viscosity can be separated in one single method step. The shear viscosity and the extensional viscosity can thereby be simultaneously determined in the same sample.

The invention has a plurality of advantages. The shear viscosity is measured over an entire shear velocity range and the extensional viscosity is determined for a well-defined average extensional velocity on the same sample and in one method step. Assumptions concerning unknown flow and/or pressure processes are thereby unnecessary. The method and the apparatus are robust and can be utilized discontinuously in a laboratory or in a continuously operating apparatus, directly during a manufacturing or processing procedure without loosing time for data determination to effect quality control or even for processing control.

The method can be realized in a simple apparatus consisting of well defined capillaries connected in series, one behind the other. The invention is described more closely with regard to embodiments and the drawings.

DESCRIPTION OF THE PREFERRED EMBODIMENT

Figure 1:
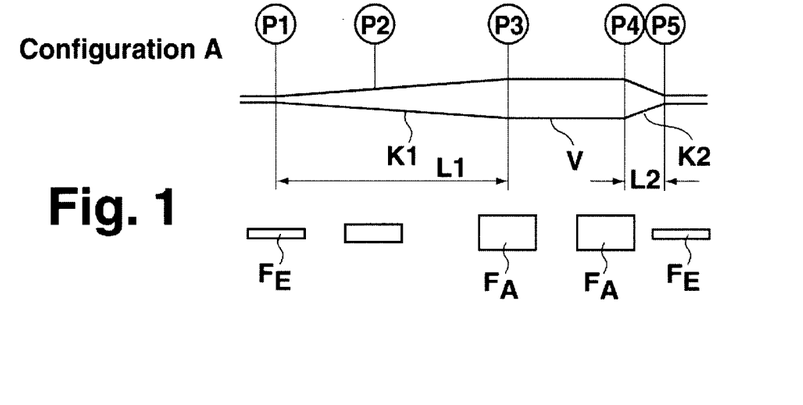
FIG. 1 shows a configuration A of two capillaries having rectangular cross sections.

FIG. 1 shows a configuration A of two capillaries K1 and K2 having differing lengths L1 and L2 and each having rectangular cross sections, wherein the capillary K1 widens in a wedge-shaped fashion from a narrow cross section $F_E$ to a wider cross section $F_A$. The capillary K1 is connected at its region of wide cross section and via a connecting member V having a constant cross section $F_A$ to the capillary K2 at its region of wide cross section, wherein the capillary K2 narrows in a wedge-shaped fashion along the length L2 into cross section $F_E$.

The capillary K1 has a pressure transducer P1 proximate its most narrow cross section, at least one pressure transducer P2 at a location along the length L1, and a pressure transducer P3 proximate the widest cross section. The capillary K2 has a pressure transducer P4 proximate the widest cross section and a pressure transducer P5 proximate the most narrow cross section.

Figure 2:
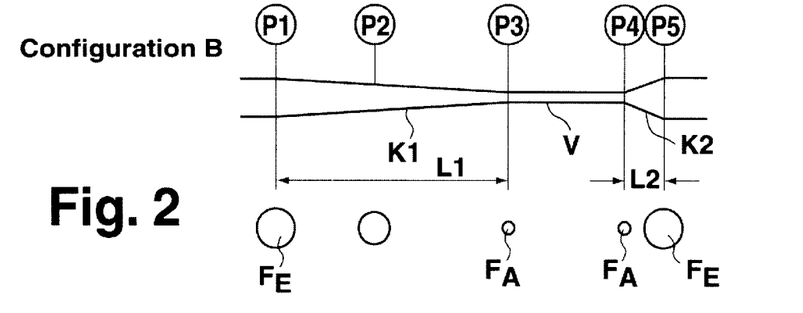
FIG. 2 shows a configuration B of two capillaries having round cross sections.

FIG. 2 shows a configuration B comprising two capillaries K1 and K2 having differing lengths L1 and L2, each having circular cross sections. The capillary K1 narrows in a conical fashion from a wide cross section $F_E$ into a narrow cross section $F_A$. The capillary K1 is connected at the narrow cross section $F_A$ and via a connecting member V having constant cross section $F_A$, to the capillary K2 at its narrow cross section $F_A$. The capillary K2 widens in a conical fashion along the length L2 into a cross section $F_E$. The capillary K1 thereby has a pressure transducer P1 proximate its widest cross section, a pressure transducer P2 at a location along its length L1 and a pressure transducer P3 proximate its most narrow section. The capillary K2 has a pressure transducer P4 proximate its most narrow cross section and a pressure transducer P5 proximate its widest cross section.

The configuration A of FIG. 1 could also have a circular cross section and the configuration B of FIG. 2 a rectangular cross section.

Figure 3A:
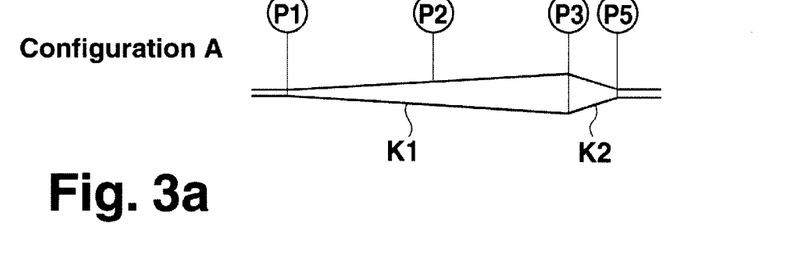
FIG. 3a shows a configuration A of two capillaries, one having a monotonically increasing cross section and the other having a monotonically decreasing cross section.

FIG. 3a shows a configuration A having a steadily widening capillary K1 and a steadily narrowing capillary K2 each having rectangular or circular cross sections. The capillaries K1 and K2 connect directly to each other at their widest cross sections, without a connecting member. The capillary K1 has a pressure transducer P1 proximate its most narrow cross section, a pressure transducer P2 at a location along the capillary, and a pressure transducer P3 directly at the transitional location between K1 and K2. The capillary K2 has a pressure transducer P5 proximate its most narrow location. The lengths of capillaries K1 and K2 differ.

Figure 3B:
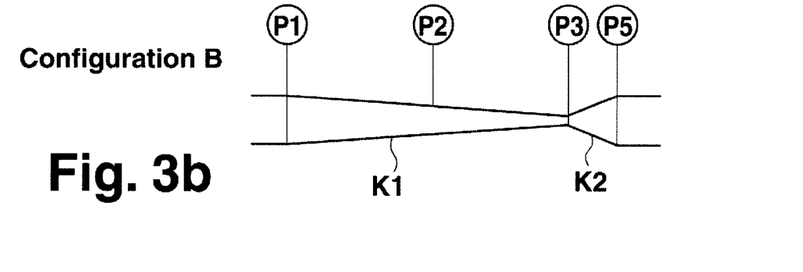
FIG. 3b shows a configuration B of two capillaries, one having a monotonically decreasing cross section and the other having a monotonically increasing cross section.

FIG. 3b shows a configuration B with a steadily narrowing capillary K1 and a steadily widening capillary K2 each having rectangular or circular cross sections. The capillaries K1 and K2 each connect directly to each other at their most narrow cross sections, without an intermediate member. The capillary K1 has a pressure transducer P1 proximate its widest cross section, a pressure transducer P2 positioned along the capillary, and a pressure transducer P3 directly at the transitional location from K1 to K2. The capillary K2 has a pressure transducer P5 proximate its widest location. The lengths of capillaries K1 and K2 differ.

Figure 4A:
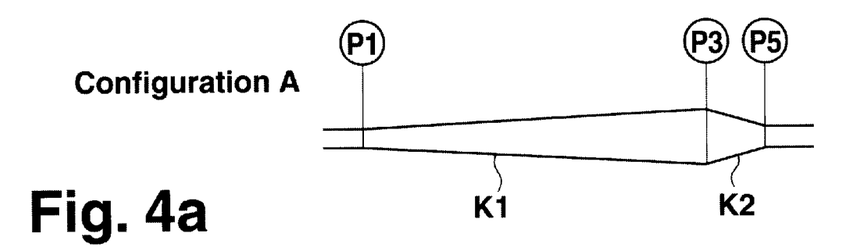
FIG. 4a shows a configuration A of two capillaries, one having an increasing cross section and one having a decreasing cross section.

FIG. 4a shows a configuration A with a continuously widening capillary K1 and a continuously narrowing capillary K2, each having rectangular or circular cross section. The capillaries K1 and K2 have differing lengths and are connected to each other at their widest cross sections without an intermediate member and the capillary K1 has a pressure transducer P1 proximate its most narrow location, and a pressure transducer P3 directly at the transitional location from K1 to K2, and the capillary K2 has a pressure transducer P5 proximate it most narrow location.

Figure 4B:
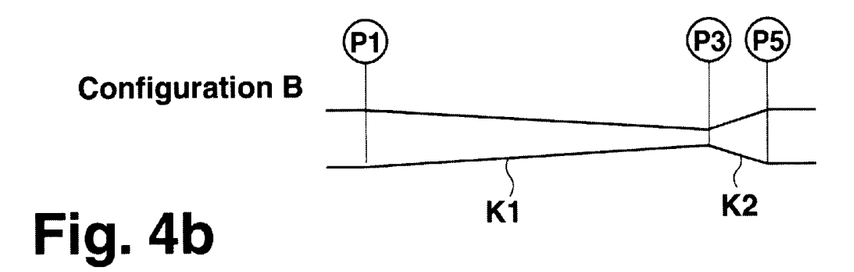
FIG. 4b shows a configuration B of two capillaries, one having a continuously narrowing cross section and one having a continuously widening cross section.

FIG. 4b shows a configuration B with a continuously narrowing capillary K1 and a continuously widening capillary K2 each having rectangular or circular cross sections, wherein the capillaries K1 and K2 connect to each other directly, without an intermediate member, at their most narrow locations. The capillary K1 has a pressure transducer P1 proximate its widest location, and a pressure transducer P3 at the transitional location between K1 and K2. The capillary K2 has a pressure transducer P5 proximate its widest location. The lengths of capillaries K1 and K2 are also different in this case.

Figure 5:
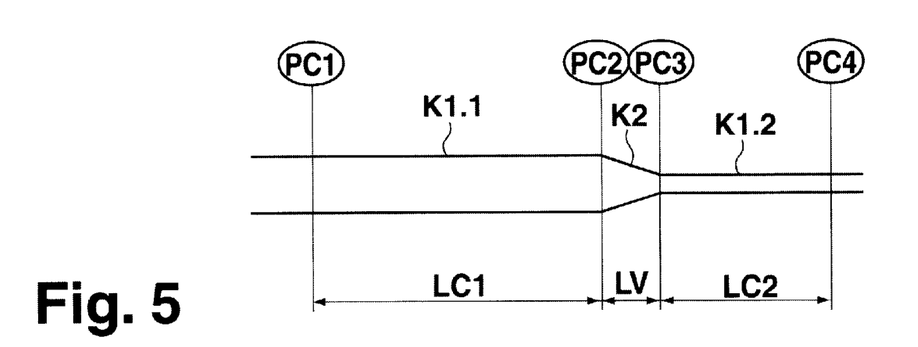
FIG. 5 shows a configuration having two capillaries each of constant but differing cross section joined by a transition member.

FIG. 5 shows a capillary K1 in the form of two partial capillaries K1.1 and K1.2 having lengths LC1 and LC2, each with rectangular or circular cross sections. Each of the cross sections of the partial capillary K1.1 along its length LC1 and of the partial capillary K1.2 along its length LC2 are constant. A transitional member is disposed between the partial capillaries K1.1 and K1.2 and has a length LV and rectangular or circular cross section respectively, and serves as a second capillary K2 having the cross section of partial capillary K1.1 proximate K1.1 and the cross section of partial capillary K1.2 proximate K1.2. The partial capillary K1.1 has a pressure transducer PC1 proximate its beginning portion and a pressure transducer PC2 proximate the transitional member K2. Partial capillary K1.2 has a pressure transducer PC3 proximate the transitional member K2 and a pressure transducer PC4 proximate its output region. More than two pressure transducers can also be disposed along the capillaries.

Figure 6:
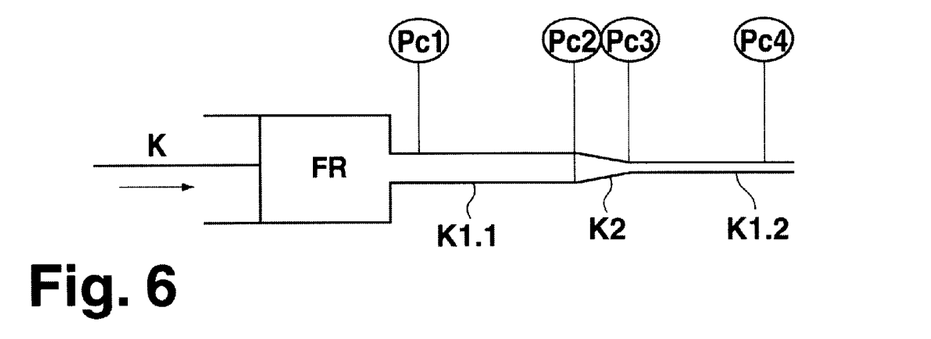
FIG. 6 shows a capillary configuration of FIG. 5, connected to a liquid reservoir having a movable piston.

FIG. 6 shows a capillary configuration in accordance with FIG. 5, connected to a liquid reservoir a having a movable piston K.

Figure 7:
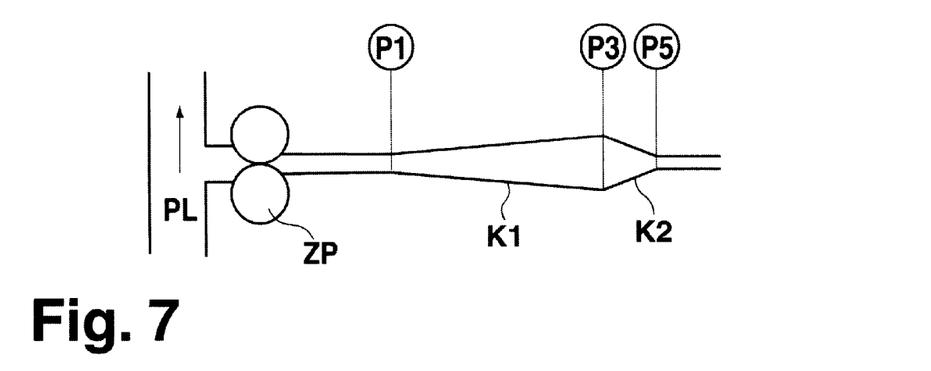
FIG. 7 shows a capillary configuration of FIG. 4a connected to a product conduit via a dosing pump.

FIG. 7 shows a capillary configuration in accordance with FIG. 4a connected to a product conduit PL via a dosing pump ZR.

Figure 8:
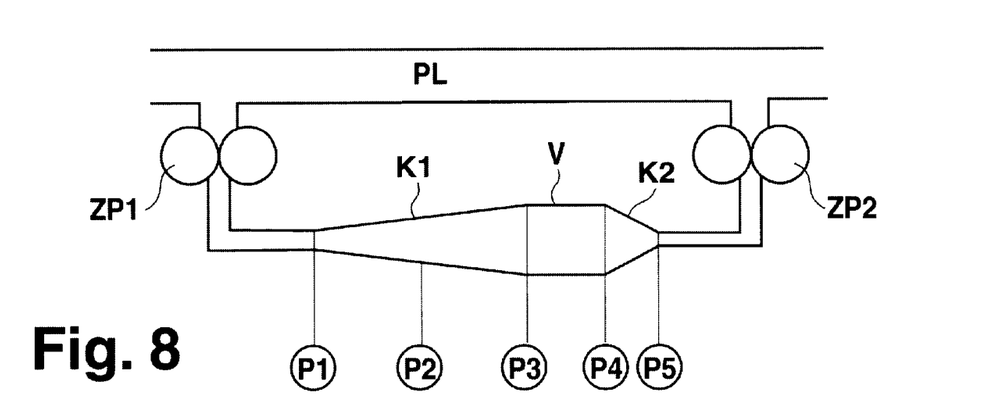
FIG. 8 shows a capillary configuration in accordance with FIG. 1, connected to a product conduit via dosing and return pumps.

FIG. 8 shows a capillary configuration in accordance with FIG. 1 connected to a product conduit via a dosing pump ZP1 and a return pump ZP2.

In the embodiment according to FIG. 1 (configuration A), two capillaries K1 and K2 have the same inlet cross sections $F_E$ and same outlet cross sections $F_A$ but are of differing lengths L1 and L2 and are directly connected, one behind the other. The cross sections can be rectangular (a wedge-shaped capillary→a planer extension) or round (a conical-shaped capillary→uniaxial extension). Both capillaries contain the same volume flow $\dot{V}$ for testing a liquid, so that the liquid in both capillaries K1 and K2 is loaded within the same shear velocity range (e.g. $\dot{\gamma}_E:\dot{\gamma}_A$=2:1 to 100:1). The longer capillary (K1 in this example) is then dimensioned in such a fashion that the extensional velocity $\dot{\epsilon}$ in accordance with equation 6 is small such that the tensile stress σ, as given by equation (4), can be neglected relative to the pressure difference P1–P3 (P1–P3>σ). These capillaries then serve for determining the shear viscosity only (see also DE 42 36 407 A1). If this capillary is equipped with at least three pressure measurement locations, in accordance with Papendinskas et al., the actual viscosity within the capillary can be determined or a potential law in accordance with equation (2) can be formulated as an approximation in the flow region between the inlet and outlet shear velocities. The capillary K2 also has input and output cross sections $F_A$ and $F_E$, but length L2 is much less than L1 (e.g. L1=20 mm to 500 mm and L2:L1=1:5 to 1:200). Since shearing in K2 is in the same shear velocity range as in capillary K1 and since capillary K2 is geometrically similar to capillary K1, the pressure drop ΔPS2 in K2 due to shearing is smaller than that in K1 by the factor L2/L1, independent of the flow function of the liquid:

$$\Delta PS2=(P1-P3)(L2/L1) \quad (7)$$

The extensional velocity in K2 is however increased in accordance with equation (6) by the factor L1/L2 compared to the extensional velocity in K1. Therefore K2 has a substantially higher fraction of extensional compared to shear resistance. This extensional resistance is contained in the pressure difference (P4–P5). Since the pure shear resistance is known through equation (7), it is possible to separate σ and the extensional viscosity $\eta_E$ from P4–P5.

$$\sigma=(P4-P5)-\Delta PS2 \quad (8)$$

In this fashion, the shear viscosity η and the extensional viscosity $\eta_E$ are determined simultaneously in the same sample. Such a device can e.g. be used for on-line monitoring during constant volume flow (inexpensive) or be operated at constant pressure difference (P1–P3) or (P4–P5). For the constant pressure operational mode, the shear viscosity η, the flow exponent n, and the extensional viscosity $\eta_E$ can be directly correlated to molecular quantities such as the average molecular weight and molecular weight distribution.

In principle, flow through the configuration of the two capillaries K1 and K2 shown in FIG. 1 can be in either direction so that a liquid element passes either first through the longer capillary K1 and then through the shorter capillary K2 or first through the shorter and then through the longer capillary.

Other embodiments are also possible with respect to the configuration of the narrow and wide capillary sections to solve the problem in accordance with the invention of providing simultaneous measurement of the shear and the extensional viscosities. Configurations in which a narrow cross section is adjacent to a wider cross section have the associated difficulty of requiring a transitional zone in which the liquid to be measured is subjected to additional deformations (e.g. through narrowing or widening of the flow channel).

In embodiments designated as configuration A in FIG. 1 and configuration B in FIG. 2, both capillaries K1 and K2 are connected to each other via a connecting member V. The liquid is loaded in this connecting member with the shear velocities associated with the output of the one capillary and the input of the other capillary. Flow is not accelerated in these connecting members and is therefore settled. The embodiments shown in FIGS. 1 and 2 can be optimally adjusted to the application and provide the possibility of determining the actual values of the shear viscosity and also of the extensional viscosity (e.g. by shaping the dependence of the narrowing of the capillary K2 in a hyperbolic manner to facilitate determination of the actual extensional velocity $\dot{\epsilon}$ and, using equation (4), the actual extensional viscosity). A device of this kind then becomes an absolute rheometer. Should such a device be operated with differing volume flows $\dot{V}$ or pressure differentials $\Delta p$, it is then possible to measure both $\eta(\dot{\gamma})$ as well as $\gamma_E (\dot{\epsilon})$.

It is not always necessary to determine actual material characteristic values in process monitoring applications. FIGS. 3a to 5 describe embodiments having a reduced amount of equipment (therefore less expensive and more robust) but which nevertheless facilitate separation of the shear viscosity values and extensional viscosity values using the method in accordance with the invention.

In FIGS. 3a and 3b, the two capillaries K1 and K2, described in FIGS. 1 and 2, are connected to each other directly without an intermediate member V in such a fashion that the outlet of the one capillary simultaneously constitutes the inlet of the other capillary. A point-like measuring transducer disposed at location P3 can be used to measure both the output pressure (or input pressure) of the capillary K1 as well as the input pressure of K2. This configuration is therefore more compact and reduces the dwell time of the test fluid and thereby the associated response time required for detecting material changes. A substantial feature is the reduction in the number of pressure measuring locations. The rheometer is smaller, less expensive and is less susceptible to failure, since it has one less pressure measuring location.

If one is willing to forfeit determination of the actual shear viscosity, it is possible to do without an additional pressure measuring location. The pressure measuring location P2 can then be removed, wherein the possibility of determining the flow exponent n is lost. In order to determine the shear viscosity from the pressure difference (P1–P3)in the capillary K1 it is then necessary to use the equations for Newtonian liquids having shear velocity independent viscosities. In this case a so-called apparent viscosity is calculated. This quantity is sufficient for many process and quality control tasks in order to characterize and properly quantify changes in the processed liquid. The separation between shear viscosities and extensional viscosities according to equation (7) and (8) is nevertheless possible, since the reduction in the pressure drop in the capillary K2, which is proportional to the length, substantially remains due to the geometrical similarity of the capillaries. FIGS. 4a and 4b show, by way of example, embodiments having only three pressure transducers. (In principle, the removal of one pressure measuring location P2 is also possible in the embodiments according to FIGS. 1 and 2).

A special application of the method in accordance with the invention for separation of shear and extensional viscosities is schematically shown in FIG. 5. In this embodiment, the partial capillaries K1.1 and K1.2 each have a constant cross section and produce a constant flow field along their axes and a constant shear velocity without additional extension. Since both partial capillaries K1.1 and K1.2 contain the same volume flow but have differing cross sections, the shear velocities also differ. Using the pressure differences (PC1–PC2) and (PC3–PC4) in conjunction with the capillary dimensioning, it is possible to calculate the shear stress $\tau_C 1$ and $\tau_C 2$ and the associated apparent shear velocities $\dot{\gamma}ap1$ and $\dot{\gamma}ap2$. In this manner, two points of the flow function are determined with which the flow exponent n characterizing this shear region can be calculated.

The connecting member K2 between these two partial capillaries K1.1 and K1.2 brings the liquid from a shear velocity $\dot{\gamma}_1$ in the partial capillary K1.2 to a shear velocity $\dot{\gamma}2$ along a short path LV. The flow within the connecting member K2 is therefore precisely delimited by the points of the flow function determined in capillaries C1 and C2 and can be described in the intermediate region by a potential function in accordance with equation (2), having exponent n. Using the conventional equations for a potential liquid and the narrowing or widening of the gap, one can calculate the pressure loss $\Delta p(LV)$ across the connecting member K2 along the length LV. The pressure difference (PC2–PC3) minus $\Delta p$ (LV) then leads to the tensile stress $\overline{\sigma}$ and, using equation (6,) the extensional velocity $\dot{\epsilon}$. The device shown in FIG. 5 can thereby separate the shear and extensional viscosities using the method described. The partial capillaries K1.1 and K1.2 thereby serve to determine the shear viscosity analogous to capillary K1 (in FIGS. 1 through 4), wherein the connecting member K2 serves the function of capillary K2.

The method described serves for simultaneous determination of the shear and the extensional viscosities of a liquid in one single sample and in one single method step. Towards this end, the shear flow behavior of a liquid within a predetermined shear velocity range is determined using a capillary having changing cross section or with a plurality of capillaries having constant cross sections. The same liquid is then subsequently pressed through a downstream second flow channel, wherein this channel is shaped in such a fashion that the liquid is subjected to the same shear velocity range between the corresponding pressure measuring locations, however the extensional flow fraction represents a substantial portion of the overall flow-through resistance compared to the shear flow fraction.

For the case of capillaries having changing cross section, this is most easily effected using capillaries having the same cross sections but largely differing lengths (similar capillaries).

Clearly, the capillary K1 can also be dimensioned to determined the shear viscosity in such a fashion that the viscosity function is determined in a larger or smaller shear velocity range than present in K2. However, the precision of the measurement normally suffers thereby and transitional elements are necessary between the output of K1 and the input of K2 which lead to the disadvantages already mentioned.

Three examples are shown in FIGS. 6 to 8 of how the device in accordance with the invention can be adapted to conventional devices to carry out the method in accordance with the invention.

In the example of FIG. 6, a capillary configuration in accordance with FIG. 5 is connected to a liquid reservoir FR having a moving piston K in such fashion that constant motion of the piston K leads to constant volume flow $\dot{V}$ of a liquid to be tested out of the liquid reservoir and through the capillary configuration. The same volume flow $\dot{V}$ is present at each location of the capillary configuration. Using the conventional equations, the volume flow $\dot{V}$, the dimensions of partial capillaries K1.1 and K1.2 as well as the pressure differences (PC1–PC2) and (PC3–PC4) can be used to determine the flow velocities and shear stresses along the partial capillaries K1.1 and K1.2. This information can then be used to calculate the viscous pressure drop across the connecting member K2 and the strain viscosity $\eta_E$ can be separated through a comparison between this calculated viscous pressure drop and the measured pressure drop PC2–PC3), in accordance with equations given. The entire method can be carried out with differing piston speeds so that differing regions of shear viscosity can be measured together with the extensional viscosities $\eta_E$ associated with differing extensional velocities $\dot{\epsilon}$. The method shown herein is particularly suitable for discontinuous laboratory investigations, wherein the liquid reservoir and the moving piston can be components within commercially available rheometers. In principle, one can also proceed in such a fashion that the motion of the piston K is controlled to establish a constant pressure drop across one of the partial capillaries K1.1 or K1.2 or across the entire capillary configuration. Differing pressure drops then lead to differing ranges of the shear viscosities and values for the extensional viscosity.

A combination of a capillary configuration e.g. in accordance with FIG. 4a and a gear pump, functioning as a dosing or a metering pump to transport the test liquid out of a product conduit and into a capillary as shown in FIG. 7, is particularly well suited for continuous processing and quality control as well as for process control. A constant volume flow $\dot{V}$ is transported through the capillary configuration using a constant rate of rotation for the dosing pump ZP. Using $\dot{V}$, the dimensions of the capillary K1 and the pressure drop (P1–P3), shear velocity and shear stress values can be determined using the equations for diverging capillaries with which the pressure drop due to the shear viscosity along the converging capillary K2 can be calculated. This can be done on-line, preferably using a computer. The difference between the viscous pressure drop calculated for the capillary K2 and the measured pressure drop (P3–P5) permits calculation of the extensional viscosity using the known equations. Different rates of revolution can be used to determine values for the shear and extensional viscosities for differing shear and extensional velocities. The material values determined in this fashion can be used for quality control and/or also be directly used to drive or regulate a process. If the apparatus is not operated at constant rate of revolution, rather in such a fashion that constant pressure drops establish themselves across sections of the capillary configuration or along the entire capillary configuration, then one can extract shear viscosity values and extensional viscosity values which can be directly correlated to molecular quantities (laid open publication DE 42 36 407). Capillary rheometers, which transport a test liquid out of a product conduit or out of a production apparatus using a gear pump and into a simple measuring capillary, are per se known in the art as by-pass rheometers.

FIG. 8 shows an example of a capillary configuration A in accordance with FIG. 1 with which a test liquid is pumped out of a product conduit PL and through the capillary configuration K1 and K2 using a dosing pump ZP1 as a metering pump, and the test liquid is then transported by means of the return pump ZP2 back into the product conduit. Such configurations of pumps and measuring capillaries are referred to as side-flow rheometers, wherein the device in accordance with FIG. 1 thereby delivers, on-line, the shear viscosity, the flow exponent and, in accordance with the invention, the extensional viscosity. Other modes of operation and processes can be carried out similarly to those already described for FIGS. 6 and 7.

I claim:

1. A method for continuous or discontinuous measurement of shear and extensional viscosities of Newtonian and non-Newtonian liquids and of structurally viscous liquids, polymer melts, elastomers solutions and other structural liquids, the method comprising the steps of:
    a) passing the liquid through a first capillary member to subject the liquid to substantially shear loads only and within a shear velocity range;
    b) measuring a first pressure difference at said first capillary member to determine a shear viscosity at at least two measuring points and a shear resistance of the liquid;
    c) passing the liquid through a second capillary member to subject the liquid to both extensional and shear loads within said shear velocity range or within a shear velocity range smaller than said shear velocity range, said second capillary member in series connection with said first capillary member;
    d) measuring a second pressure difference at said second capillary member to measure a flow-through resistance of said second capillary member, said flow-through resistance comprising both said shear resistance and a extensional resistance;
    e) subtracting a portion pressure difference from said second pressure difference, said portion of pressure difference corresponding to said shear resistance as determined in step b); and
    f) separating said extensional viscosity as defined by the remaining calculated value that results from following step e).

2. The method of claim 1, further comprising keeping a volume flow constant.

3. The method of claim 1, further comprising keeping an overall pressure difference constant.

4. The method of claim 1, further comprising keeping a pressure difference along one said first and said second capillary members constant.

5. The method of claim 1, further comprising keeping a pressure difference constant along a partial region of one of said first and said capillary members.

6. The method of claim 1, wherein said first and said second capillary members are tapered.

7. The method of claim 6, wherein said first and said second capillary members have one of a round and a rectangular cross section.

8. The method of claim 1, further comprising the step of:
    b1) passing the liquid through a connecting member disposed between and connecting said first capillary member and said second capillary member.

9. The method of claim 7, wherein capillary ends having a widest cross section are connected to each other.

10. The method of claim 7, wherein capillary ends having a narrow cross section are connected to each other.

11. The method of claim 1, wherein at least one of said first pressure difference and said second pressure difference is determined in at least two capillary sections of a particular capillary member.

12. The method of claim 6, wherein said first capillary member has a first end having a first cross section and a second end having a second cross section and wherein said second capillary member has a first end having a first cross section and a second end having a second cross section, wherein said first capillary member first cross section equals said second capillary member first cross section and wherein said first capillary member second cross section equals said second capillary member second cross section.

13. The method of claim 1, wherein said first capillary member has first length L1 said second capillary member has a second length L2, wherein $2 \leq L1/L2 \leq 200$.

14. The method of claim 6, wherein said first capillary member has a first end having a first cross section FE1 and a second end having a second cross section FA1 and wherein said second capillary member has a first end having a first cross section FE2 and a second end having a second cross section FA2, wherein $FA1/FE1 \neq FA2/FE2$.

15. The method of claim 6, wherein said first capillary member is directly connected to said second capillary member, without an intermediate member.

16. The method of claim 1, wherein a pressure is measured directly at a connecting location between said first and said second capillary members.

17. The method of claim 1, wherein only an overall pressure difference across each of said first and said second capillary members is determined.

18. The method of claim 1, wherein a pressure on an outside end of said first capillary member, a pressure on a connecting location between said first and said second capillary members and a pressure on an outside end of said second capillary are determined.

19. The method of claim 1, wherein said first capillary member consists essentially of a first partial capillary having a first constant cross section and a second partial capillary having a second constant cross section not equal to said first constant cross section, wherein said second capillary member is connected between said first and said second partial capillaries to transfer the liquid from one of said first and said second partial capillaries into an other of said first and said partial capillaries.

20. The method of claim 19, wherein a pressure drop across said first partial capillary, up to an input end of said second capillary member and a pressure drop across said second partial capillary, downstream of an output of said second capillary member, are determined.

21. An apparatus for continuous or discontinuous measurement of shear and extensional viscosities of Newtonian and non-Newtonian liquids and of structurally viscous liquids, polymer melts, elastomers solutions and other structural liquids, the apparatus comprising:
a first capillary member having a first pitch defining a cross section which continuously widens in a flow direction;
a second capillary member, disposed downstream of said first capillary member, said second capillary member having a second pitch defining a cross section which continuously narrows in said flow direction, said second pitch differing from said first pitch;
a first pressure sensor disposed at said first capillary member;
a second pressure sensor disposed at said first capillary member downstream of said first pressure sensor;
a third pressure sensor disposed at said second capillary member; and
a fourth pressure sensor disposed at said second capillary member downstream of said third pressure sensor.

22. The apparatus of claim 21, further comprising an intermediate member connected between said first and said second capillary members.

23. The apparatus of claim 21, wherein said first and said second capillary members are disposed immediately following one another.

24. The apparatus of claim 21, wherein an input cross section of said first capillary member is equal to an output cross section of said second capillary member.

25. The apparatus of claim 21, wherein said first capillary member has a first length L1 and said second capillary member has a length L2, wherein $2 \leq L1/L2 \leq 200$.

26. The apparatus of claim 21, further comprising a first liquid reservoir from which the liquid can be transported through said first and said second capillary members with one of constant volume flow and an adjustable constant pressure.

27. The apparatus of claim 21, further comprising a dosing pump for transporting liquid out of an external system with one of an adjustable volume flow and an adjustable pressure and through said first and said second capillary members, wherein the liquid is expelled after passing through said first and said second capillary members.

28. The apparatus of claim 21, further comprising an additional pressure sensor disposed at one of said first and said second capillary members downstream of one of said second and said fourth pressure sensors.

29. An apparatus for continuous or discontinuous measurement of shear and extensional viscosities of Newtonian and non-Newtonian liquids and of structurally viscous liquids, polymer melts, elastomers solutions and other structural liquids, the apparatus comprising:
a first capillary member having a cross section which continuously narrows in a flow direction;
a second capillary member, disposed downstream of said first capillary member, said second capillary member having a cross section which continuously widens in said flow direction;
a first pressure sensor disposed at said first capillary member;
a second pressure sensor disposed at said first capillary member downstream of said first pressure sensor;
a third pressure sensor disposed at said second capillary member;
a fourth pressure sensor disposed at said second capillary member downstream of said third pressure sensor; and
a dosing pump for transporting liquid out of an external system with one of an adjustable volume flow and an adjustable pressure and through said first and said second capillary members, wherein the liquid is expelled after passing through said first and said second capillary members.

30. An apparatus for continuous or discontinuous measurement of shear and extensional viscosities of Newtonian and non-Newtonian liquids and of structurally viscous liquids, polymer melts, elastomers solutions and other structural liquids, the apparatus comprising:
a first capillary member having a cross section which continuously narrows in a flow direction;

a second capillary member, disposed downstream of said first capillary member, said second capillary member having a cross section which continuously widens in said flow direction;

a first pressure sensor disposed at said first capillary member;

a second pressure sensor disposed at said first capillary member downstream of said first pressure sensor;

a third pressure sensor disposed at said second capillary member;

a fourth pressure sensor disposed at said second capillary member downstream of said third pressure sensor;

a dosing pump to transport the liquid with one of adjustable volume flow and adjustable pressure, out of an external system and through said first and second capillary members; and a second pump disposed at an output of said first and said second capillary members to transport the liquid back into the external system.

31. An apparatus for continuous or discontinuous measurement of shear and extensional viscosities of Newtonian and non-Newtonian liquids and of structurally viscous liquids, polymer melts, elastomers solutions and other structural liquids, the apparatus comprising:

a first capillary member having a cross section which continuously narrows in a flow direction;

a second capillary member, disposed downstream of said first capillary member, said second capillary member having a cross section which continuously widens in said flow direction;

a first pressure sensor disposed at said first capillary member;

a second pressure sensor disposed at said first capillary member downstream of said first pressure sensor;

a third pressure sensor disposed at said second capillary member;

a fourth pressure sensor disposed at said second capillary member downstream of said third pressure sensor; and an additional pressure sensor disposed at one of said first and said second capillary members downstream of one of said second and said fourth pressure sensors.

32. An apparatus for continuous or discontinuous measurement of shear and extensional viscosities of Newtonian and non-Newtonian liquids and of structurally viscous liquids, polymer melts, elastomers solutions and other structural liquids, the apparatus comprising:

a first capillary member consisting essentially of a first partial capillary having a first constant cross section and a second partial capillary disposed downstream of said first partial capillary and having a second constant cross section;

a connecting member disposed between said first and said second capillaries and forming a second capillary member having a cross section which continuously changes from said first constant cross section to said second constant cross section;

a first pressure sensor disposed at said first partial capillary;

a second pressure sensor disposed at said first partial capillary member downstream of said first pressure sensor;

a third pressure sensor disposed at said second partial capillary;

a fourth pressure sensor disposed at said second partial capillary downstream of said third pressure sensor; and a dosing pump for transporting liquid out of an external system with one of an adjustable volume flow and an adjustable pressure and through said first and said second capillary members, wherein the liquid is expelled after passing through said first and said second capillary members.

33. An apparatus for continuous or discontinuous measurement of shear and extensional viscosities of Newtonian and non-Newtonian liquids and of structurally viscous liquids, polymer melts, elastomers solutions and other structural liquids, the apparatus comprising:

a first capillary member consisting essentially of a first partial capillary having a first constant cross section and a second partial capillary disposed downstream of said first partial capillary and having a second constant cross section;

a connecting member disposed between said first and said second capillaries and forming a second capillary member having a cross section which continuously changes from said first constant cross section to said second constant cross section;

a first pressure sensor disposed at said first partial capillary;

a second pressure sensor disposed at said first partial capillary member downstream of said first pressure sensor;

a third pressure sensor disposed at said second partial capillary;

a fourth pressure sensor disposed at said second partial capillary downstream of said third pressure sensor;

a dosing pump to transport the liquid with one of adjustable volume flow and adjustable pressure out of an external system and through said first and said second capillary members; and a second pump disposed at an output of said first and said second capillary members to transport the liquid back into the external system.

* * * * *

UNITED STATES PATENT AND TRADEMARK OFFICE
CERTIFICATE OF CORRECTION

PATENT NO. : 6,386,016 B1
DATED : May 14, 2002
INVENTOR(S) : Gleissle, Wolfgang

It is certified that error appears in the above-identified patent and that said Letters Patent is hereby corrected as shown below:

<u>Column 7,</u>
Line 30, please replace: " $\gamma_E(\bar{\varepsilon})$ " with -- $\eta_E(\bar{\varepsilon})$ --.

Signed and Sealed this

Nineteenth Day of November, 2002

*Attest:*

*Attesting Officer*

JAMES E. ROGAN
*Director of the United States Patent and Trademark Office*